United States Patent
Coop et al.

(10) Patent No.: US 9,422,302 B2
(45) Date of Patent: Aug. 23, 2016

(54) MIXED μ AGONIST/ δ ANTAGONIST OPIOID ANALGESICS WITH REDUCED TOLERANCE LIABILITIES AND USES THEREOF

(71) Applicants: UNIVERSITY OF MARYLAND, BALTIMORE, Baltimore, MD (US); WEST VIRGINIA UNIVERSITY, Morgantown, WV (US)

(72) Inventors: Andrew Coop, Baltimore, MD (US); Alexander D. Mackerell, Baltimore, MD (US); Rae Matsumoto, Morgantown, WV (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 14/772,592

(22) PCT Filed: Mar. 6, 2014

(86) PCT No.: PCT/US2014/021155
§ 371 (c)(1),
(2) Date: Sep. 3, 2015

(87) PCT Pub. No.: WO2014/138378
PCT Pub. Date: Sep. 12, 2014

(65) Prior Publication Data
US 2016/0016965 A1    Jan. 21, 2016

Related U.S. Application Data

(60) Provisional application No. 61/774,128, filed on Mar. 7, 2013.

(51) Int. Cl.
*A61K 31/485* (2006.01)
*C07D 489/08* (2006.01)
*C07D 489/02* (2006.01)

(52) U.S. Cl.
CPC ............ *C07D 489/08* (2013.01); *C07D 489/02* (2013.01)

(58) Field of Classification Search
USPC ........................................ 514/282; 546/45, 44
See application file for complete search history.

(56) References Cited

PUBLICATIONS

Gyulai, Z. et al.: Synthesis and opioid activity of novel 6-ketolevorphanol derivatives. Medicinal Chem., vol. 9, pp. 1-10, Feb. 2013.*

* cited by examiner

*Primary Examiner* — Charanjit Aulakh
(74) *Attorney, Agent, or Firm* — Westerman, Hattori, Daniels & Adrian, LLP

(57) ABSTRACT

An opioid narcotics used for the treatment of moderate-to-severe pain that primarily exert their analgesic effects through μ receptors. Although, traditional μ agonists can cause undesired side effects, including tolerance, addition of δ antagonists can attenuate said side effects. The present invention includes 4a,9-dihydroxy-7a-(hydroxymethyl)-3-methyl-2,3,4,4a,5,6-hexahydro-1H-4,12-methanobenzofuro[3,2-e]isoquinolin-7(7aH)-one (UMB 425) a 5,14-bridged morphinan-based orvinol precursor, along with analogs of morphine, dihydromorphine, hydromorphone, codeine, dihydrocodeine, hydrocodone and ethylmorphine. Although UMB 425 lacks δ-specific motifs, conformationally sampled pharmacophore models for μ and δ receptors predict it to have efficacy similar to morphine at μ receptors and similar to naltrexone at δ receptors, due to the compound sampling conformations in which the hydroxyl moiety interacts with the receptors similar to orvinols. UMB 425 exhibits a mixed μ agonist/δ antagonist profile as determined in receptor binding. UMB 425 has mixed μ agonist/δ antagonist properties in vitro that translate to reduced tolerance liabilities in vivo.

13 Claims, 7 Drawing Sheets

(a) n-BuLi, ethyl chloroformate, THF, -78 °C, 4h, 64%; (b) LiAlH$_4$, THF, 0 °C - rt, 2h, 81%; (c) H$_2$O$_2$, HCOOH, H$_2$SO$_4$, 4 °C, 70h, 61%; (d) 10% Pd/C, H$_2$, 1:1 ethanol-glacial acetic acid, 4h, 70%; (e) BBr$_3$, CHCl$_3$, 0 °C, 3h, 64%.

Compounds included in the δ receptor CSP training set. Pharamcophoric descriptors are designated in colors where green represents an aromatic ring (A), blue a basic nitrogen (N) and red a hydrophobic group (B).

R=Me (Oxycodone analog)
R₁=Oalkyl, halogen, Nalkyl, amide, alkyl

UMB425 (oxymorphone derivative)

Analogs of morphine (R=H), codeine (R=Me), and ethylmorphine (R=Et)

Analogs of dihydromorphine (R=H) and dihydrocodeine (R=Me)

Hydrocodone (R=Me) and hydromorphone (R=H) analogs

MIXED μ AGONIST/ δ ANTAGONIST OPIOID ANALGESICS WITH REDUCED TOLERANCE LIABILITIES AND USES THEREOF

CROSS REFERENCE

This application claims benefit of U.S. Provisional Application No. 61/774,128 filed on Mar. 7, 2013, which is herein incorporated by reference.

STATEMENT OF FEDERALLY SPONSORED RESEARCH

This invention was made with government support under grant DA 13583 awarded by the National Institutes of Health. The government has certain rights in the invention.

BACKGROUND OF THE INVENTION

Tolerance develops to clinically used opioids that lead to increased doses to keep the patient in a pain-free state. As dose increases, so do undesired side effects. The present invention is based on the knowledge that delta opioid antagonists co-administered with mu agonists lessen the development of tolerance to the mu agonists (like morphine). The method comprises a new opioid analgesic (NCE) to which tolerance to analgesia develops less rapidly than morphine. The NCE has an alcohol incorporated into the 5-position of oxymorphone to give a novel compound that has the profile of a single compound with a profile of a delta antagonist and a mu agonist, and demonstrated lower tolerance than morphine in mice. This NCE, along with analogs of morphine, dihydromorphine, hydromorphone, codeine, dihydrocodeine, hydrocodone and ethylmorphine described herein, may become utilized as new analgesics with far fewer side effects than current employed opioids (morphine, oxycodone).

BRIEF SUMMARY OF THE INVENTION

The present invention relates to opioid narcotics used for the treatment of moderate-to-severe pain that primarily exert their analgesic effects through μ receptors. Although, traditional μ agonists can cause undesired side effects, including tolerance, addition of δ antagonists can attenuate said side effects. The opioid narcotics comprise 4a,9-dihydroxy-7a-(hydroxymethyl)-3-methyl-2,3,4,4a,5,6-hexahydro-1H-4,12-methanobenzofuro[3,2-e]isoquinolin-7(7aH)-one (UMB 425) a 5,14-bridged morphinan-based orvinol precursor synthesized from thebaine. Although UMB 425 lacks δ-specific motifs, conformationally sampled pharmacophore models for μ and δ receptors predict it to have efficacy similar to morphine at μ receptors and similar to naltrexone at δ receptors, due to the compound sampling conformations in which the hydroxyl moiety interacts with the receptors similar to orvinols.

In a related aspect, UMB 425 exhibits a mixed μ agonist/δ antagonist profile as determined in receptor binding and [$^{35}$S] GTPγS functional assays in CHO cells. In vivo studies in mice show that UMB 425 displays potent antinociception in the hot plate and tail-flick assays.

In another related aspect, UMB 425 has mixed μ agonist/δ antagonist properties in vitro that translate to reduced tolerance liabilities in vivo even in the absence of δ-specific motifs fused to the C-ring. Further described herein is the identification, design and characterization of novel opioid narcotics (UMB 425, analogs of morphine, dihydromorphine, hydromorphone, codeine, dihydrocodeine, hydrocodone and ethylmorphine). See, for example, FIG. 7.

Opioid analgesics, including morphine, are the traditional standards for individuals suffering from cancer pain, postoperative pain or pain from other severe trauma (1). The prescription of opioids has risen significantly since the early 1980's (2). While opioids may be the standard for treating moderate-to-severe pain, the side effects, including respiratory depression, tolerance, physical/psychological dependence, constipation, sedation, nausea/vomiting and dizziness can be problematic (3). These severe side effects often lead to the under treatment of chronic pain and increase the possibility of death (4). Therefore, there is a pressing need to identify pharmacological agents that maintain potent analgesic properties, while eliminating the problematic side effects.

Opioid receptors are G-protein coupled receptors (5) located in the central nervous system, peripheral nervous system and gastrointestinal tract (6). To date, three opioid receptor subtypes have been identified: mu (μ) (7), delta (δ) (8) and kappa (κ) (9). Traditional opioid analgesics exert their pain-relieving properties through μ receptors located within the central nervous system (10). Opioid interactions at the δ receptor have shown synergistic analgesic effects in combination with activation of the μ receptor (11). However, research suggests that the activation of the δ receptor may play a role in the side effect liabilities associated with chronic opioid use, including tolerance (12). Selective δ antagonists can reduce tolerance when given in conjunction with the traditional μ agonists, including morphine (12, 13) and opioid peptides that display mixed μ agonist/δ antagonist activity have reduced tolerance liabilities compared to traditional opioid analgesics (14).

The identification of non-peptidic opioid analgesics that display dual characteristics of μ agonism/δ antagonism could convey therapeutic advantages compared to peptides, with regards to ease of administration and delayed metabolic breakdown. Several approaches towards this goal have been undertaken, specifically the characterization of bivalent and bifunctional opioid ligands. Portoghese et al. introduced the concept of bivalent ligands, compounds that embody two specific pharmacophores connected via an optimized linker (15). Bivalent ligands containing both μ agonist and δ antagonist motifs were shown to exhibit greater analgesic effects, while also reducing tolerance and physical dependence liabilities (16). Recent evidence citing the existence of homo- and hetero-oligomeric opioid receptor complexes, including a μ-δ complex (17), suggest that bivalent opioid ligands are a viable pharmacological tool. However, certain pharmacological characteristics can be problematic for bivalent ligands, including high molecular weights and poor pharmacokinetic profiles (18).

Bifunctional ligands are based on a single pharmacophore intended to target two binding sites with functional activity distinct for each of the respective sites (19), ideally circumventing the problematic characteristics associated with bivalent ligands. Such ligands include structural motifs that are seen in traditional μ agonists as well as δ antagonists. Bifunctional ligands depicting mixed μ agonism/δ antagonism have displayed potent analgesic activity with reduced side effect liabilities, including tolerance (20). However, those developed are traditionally characterized in vivo by intracebroventricular administration, a method unsuitable for wide spread therapeutic use.

The present invention includes the synthesis, modeling and pharmacological characterization of the novel opioid ligand, 4a,9-dihydroxy-7a-(hydroxymethyl)-3-methyl-2,3,4,4a,5,6-hexahydro-1H-4,12-methanobenzofuro[3,2-e]isoquinolin-7

(7aH)-one (UMB 425). UMB 425 was originally designed by the inventors as a precursor to a series of bifunctional 5,14-bridged morphinan-based orvinols. The compound has a novel and unique structure, such that it exhibits no δ-specific motifs fused to the C-ring, and the 5'-hydroxymethyl substituent is the only functional group that distinguishes UMB 425 from the chemical structure of oxymorphone. Application of conformationally sampled pharmacophore (CSP) models of μ agonism and δ antagonism (21-23), with the latter updated as part of the present study, predicted mixed μ agonist/δ antagonist effects for UMB 425. Moreover, analysis of the conformations of UMB 425 generated as part of the CSP protocol showed that the 5'-hydroxymethyl moiety can spatially overlap with the hydroxyl group linked to the C19 of orvinols. Since some orvinols, such as buprenorphine, act as mixed μ agonist/δ antagonists (24), it was hypothesized that UMB 425 may also interact with the receptors in a similar way as the orvinols, despite UMB 425's lack of the classical δ antagonist motif on the C-ring. Indeed, in vitro and in vivo pharmacological characterization of UMB 425 show it to have high affinity and the desired μ agonism and δ antagonism profile in CHO cells, and to have antinociceptive effects with decreased development of tolerance in mice.

DESCRIPTION OF THE DRAWINGS

FIG. 1 (*b*). Probability distributions of the basic N to oxygen.

FIG. 1 (*c*). The basic N—C9-oxygen angle from the simulations used in CSP model development for etorphine (solid line), buprenorphine (dashed line), diprenorphine (dashed line) and UMB 425 (dashed line).

FIG. 2 (*b*). Dose- and time-response curves for s.c. morphine in the tail-flick assay.

FIG. 2 (*c*). Dose- and time-response curves for s.c. UMB 425 in the hot plate assay.

FIG. 2 (*d*). Dose- and time-response curves for s.c. UMB 425 in the tail-flick assay. (Acute dose- and time-response curves for s.c. morphine and UMB 425 treatment for the hot plate and tail-flick assays. Male, Swiss-Webster mice were treated with morphine (0.1-20 mg/kg, s.c.) or UMB 425 (0.1-20 mg/kg, s.c.). Latencies were recorded 30 min after drug administration and every 20 min thereafter for 150 or 210 min).

FIG. 3 (*a*). Antagonism of UMB 425 antinociception in the hot plate assay by naloxone, but not nor-BNI. * $p<0.05$.

FIG. 3 (*b*). Antagonism of UMB 425 antinociception in the tail-flick assay by naloxone, but not nor-BNI. *** $p<0.001$.

FIG. 4 (*a*). Antinociceptive tolerance development in the hot plate assay. ** $p<0.01$ vs. Morphine Day 1/UMB 425 Day 1; # $p<0.05$ vs. Morphine Day 4; ### $p<0.001$ vs. Morphine Day 5.

FIG. 4 (*b*). Antinociceptive tolerance development in the tail-flick assay. * $p<0.05$, ** $p<0.01$ vs. Morphine Day 1; # $p<0.05$ vs. Morphine Day 5.

DETAILED DESCRIPTION OF THE INVENTION

Figure 1:
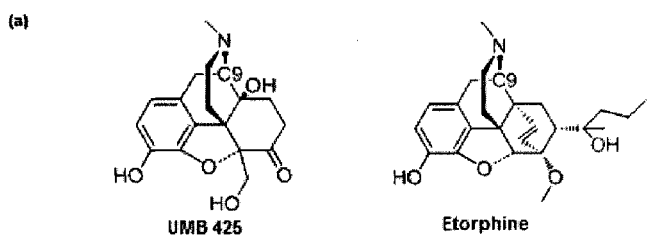
FIG. 1 (*a*). Images of UMB 425 and etorphine with the hydroxyl oxygen highlighted in red.
Figure 1:
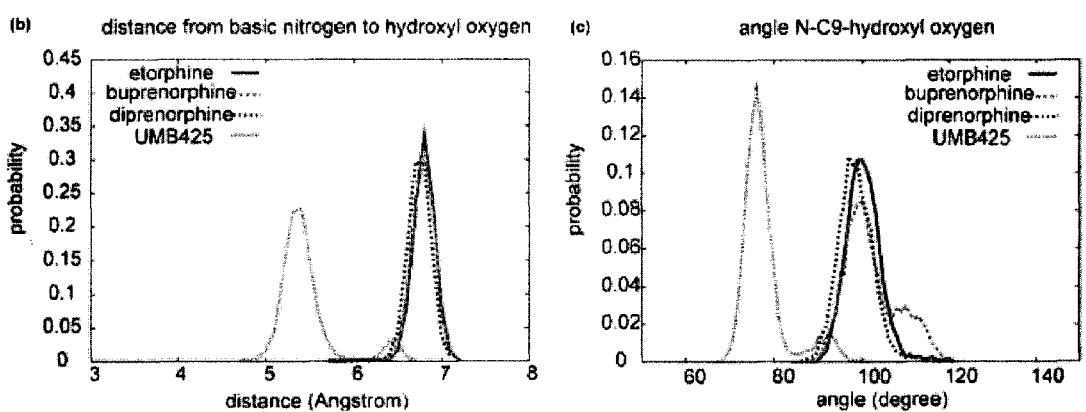

The development of novel opioid ligands with mixed μ agonist and δ antagonist activity has therapeutic potential for the treatment of pain with a lower side effect liability than commonly marketed opioid analgesics. Towards this goal a number of peptidic as well as bivalent and bifunctional non-peptidic ligands have been developed that achieve this desired pharmacological profile, but have inherent problems that limit their potential as therapeutic agents. The present invention includes UMB 425, a novel opioid that lacks a typical δ-selective motif, yet exhibits mixed μ agonist/δ antagonist activity, robust antinociceptive effects, and a reduced tolerance liability compared to morphine.

Synthesis.

A highly efficient method for the synthesis of UMB 425 is summarized in Scheme 1. Briefly, deprotonation of thebaine (1) followed by in situ reaction of the anion with ethyl chloroformate yielded 5-carbethoxythebaine (2) (25). Reduction of the ester (2) with lithium aluminum hydride gave 5-(hydroxymethyl) thebaine (3) (26). By oxidation of 5-(hydroxymethyl) thebaine (3) with a mixture of formic acid and hydrogen peroxide at 4° C. (70 h), 5-(hydroxymethyl)-14-hydroxycodeinone (4) (27) was obtained, which was reduced by catalytic hydrogenation to obtain olefin reduced diol (5). O-demethylation of the diol (5) by using boron tribromide/chloroform gave 5-(hydroxymethyl)-14-hydroxymorphinone (UMB 425) at a 64% yield (28).

μ Agonism/δ Agonism Dual-Profile CSP Model.

Prediction of the efficacy of UMB 425 applied previously developed μ agonism (21) and δ agonism (22, 23) CSP models, with the latter updated to include a larger number of non-peptidic opioid δ ligands. CSP updated δ model generation involved development of multiple individual models based on different pharmacophoric descriptors (Figure S1, supporting information); the top five models of the updated δ CSP are listed in Table 1, each with an $R^2$ greater than 0.90. The final CSP model is based on averaging the predicted efficacies from these top five models. From the model, overlap of the aromatic ring (A) to hydrophobic group (B) distance distributions was identified as the most important descriptor. AB distances of compounds showing agonism at δ opioid receptors had greater overlap with those of (±)-4-((α-R*)-α-((2S*,5R*)-4-allyl-2,5-dimethyl-1-piperazinyl)-3-hydroxybenzyl)-N,N-diethyl-benzamide (BW373U86) than antagonists; however, efficacy was explained not solely by the AB distance, but in combination with the relative position of the hydrophobic group with respect to the aromatic ring and basic N. Accordingly, overlap coefficients of angles ANB, BAN, and ABN were identified as important descriptors by the automated variable selection applied during model construction.

Calculated efficacies for the training set molecules are shown in Table 2 together with experimental values reported previously (29). The model predicts buprenorphine to be a weak partial agonist at δ receptors due to its resemblance to etorphine, particularly with respect to the AB distances. Oxymorphindole and natrindole were not differentiated by the model. The only difference between them is the N-substituent (N-methyl for oxymorphindone and N-cyclopropylmethyl for naltrindole) and the present model did not include the N-substituent as a pharmacophoric descriptor because the length of the N-substituent is not as critical for the δ receptor as it is for the μ receptor. However, the weak partial agonism of oxymorphindole seems to be due to the short methyl N-substituent.

The CSP models for the μ and δ receptor ligands were applied to UMB 425, as well as all ligands being developed as part of our ongoing research program. Predicted efficacy (% $E_{max}$) values for UMB 425 were 101 and 1.4 for the μ and δ receptors, respectively. The high efficacy at μ receptors is consistent with the structural similarity of UMB 425 with morphine or oxymorphone, while the low efficacy at δ receptors is consistent with the C-ring substituents of naltrexone.

To better understand the contribution of the 5'-hydroxymethyl to efficacy, additional analysis was performed on conformations of UMB 425 generated during CSP model development. Distances and angle distributions between the basic nitrogen and oxygen in the 5'-hydroxymethyl in UMB 425 or the 19-hydroxyl substituent in the orvinols were calculated and compared. FIG. 1 shows N—O distance and N—C9-O angle probability distributions of three orvinols and UMB 425. In FIG. 1a, two large distributions are present that are separated by around 1.5 Å, although a small peak is noted in the UMB 425 distribution at 6.5 Å that overlaps with that of the orvinols. The N—C9-O angle indicates the relative position of the hydroxyl group with respect to the plane of the aromatic A-ring. The hydroxyl group of UMB 425 is slightly above the A-ring plane while that of the orvinols is below; however, a small overlap between UMB 425 and the orvinols is observed (FIG. 1b). While preliminary, these results indicate that UMB 425 can assume conformations in which its hydroxyl moiety participates in interactions with the receptors that are similar to those occurring with the orvinols. The recent availability of X-ray crystal structures of the μ and δ receptors will allow for future evaluation of the present model in the context of 3D interactions between UMB 425, as well as other ligands, and the receptors (30, 31).

Opioid Receptor Binding Affinities.

UMB 425 demonstrates greater selectivity for the μ receptor than either the δ receptor or the κ receptor. Table 3 summarizes the binding of UMB 425 and morphine at human μ, δ and κ opioid receptors stably transfected into and overexpressed in CHO cells. Consistent with previous reports, morphine has higher binding affinity for the μ receptor to that of the δ receptor and the κ receptor (δ/μ=51; κ/μ=41). UMB 425 also has high binding affinity for the μ receptor with preference for it compared to both the δ receptor and the κ receptor (δ/μ=65; κ/μ=66).

Functional Assays for Agonist and Antagonist Activity.

Agonist and antagonist activities for morphine and UMB 425 at each of the human opioid receptor subtypes overexpressed in CHO cells are summarized in Table 3. For the [$^{35}$S]GTPγS functional assay, UMB 425 displayed comparable partial agonistic capabilities at the μ receptor to that of morphine ($EC_{50}$=35±3.7 and 38±4.9 nM; % $E_{max}$=73±7.3 and 81±2.3 nM for UMB 425 and morphine respectively). Unlike morphine, which is highly efficacious at the δ receptor ($EC_{50}$=316.5±4.9 nM; % $E_{max}$=103±7) (32), UMB 425 displayed no significant agonist activity through the δ or κ receptors, yet it did demonstrate antagonistic activity through the δ receptor indicated by a corresponding $pA_2$ value of 6.12 (−0.91).

Acute Antinociceptive Effects.

Figure 2:
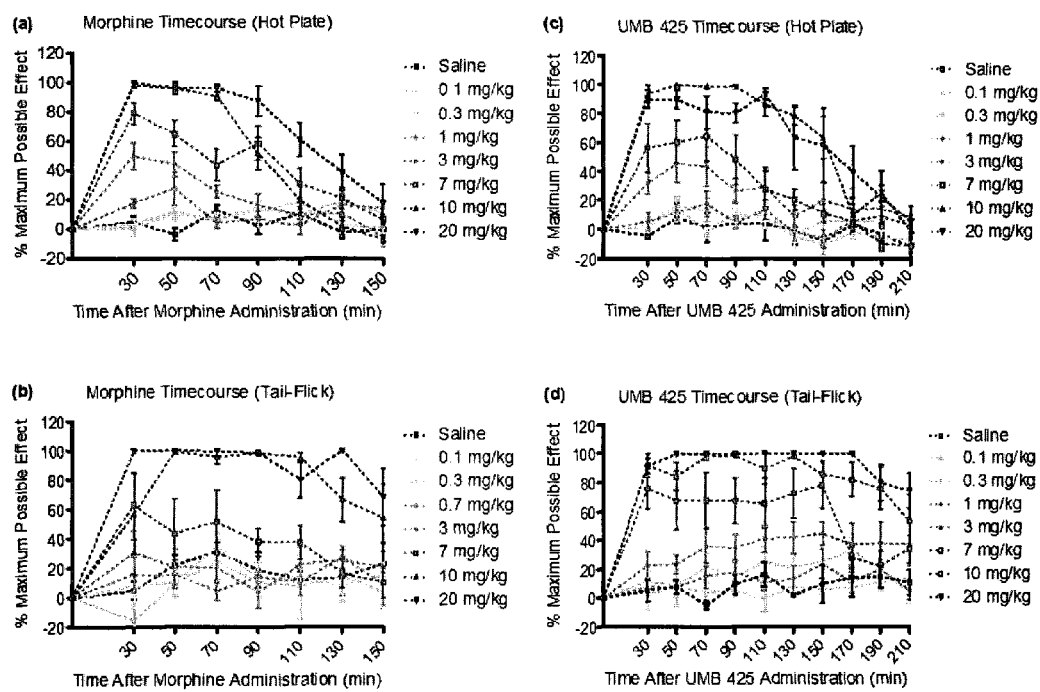
FIG. 2 (*a*). Dose- and time-response curves for s.c. morphine in the hot plate assay.

Subcutaneous injection of morphine or UMB 425 demonstrated antinociceptive effects in mice in a time- and dose-dependent manner for the thermal nociceptive assays (FIG. 2). Maximal antinociceptive responses were elicited at similar doses for both drugs. Table 4 summarizes respective $ED_{50}$ values for morphine and UMB 425 from testing performed 30 min after drug treatment. The potency of the antinociceptive activity of UMB 425 ($ED_{50}$=4.30 and 8.83 mg/kg for the hot plate and tail-flick assays, respectively) was similar to morphine ($ED_{50}$=2.73 and 6.85 mg/kg for the hot plate and tail-flick assays, respectively).

Opioid Antagonism.

Figure 3:
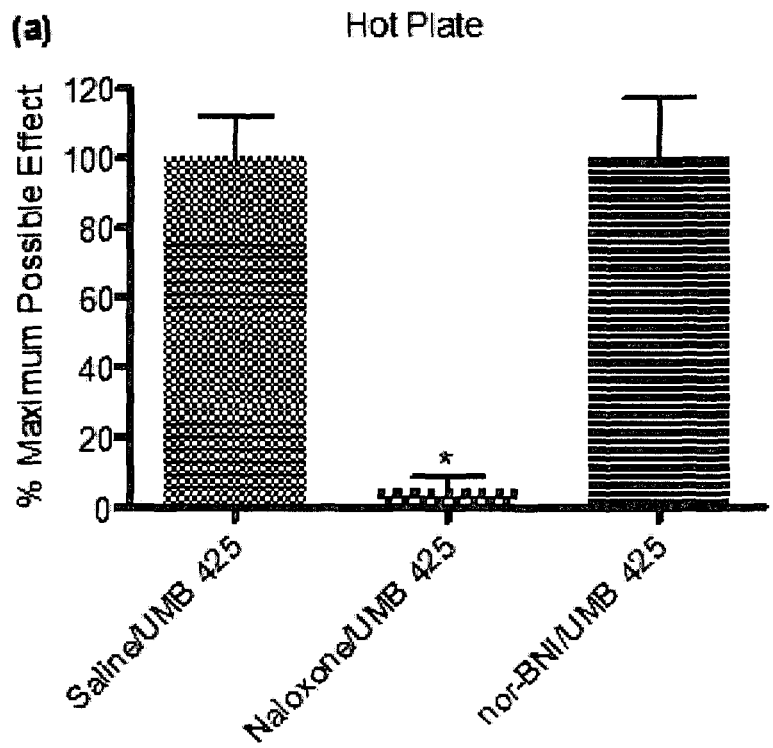
FIG. 3. Antagonism of UMB 425 antinociception using various opioid antagonists. Male, Swiss Webster mice received a pre-treatment of the non-selective opioid antagonist, naloxone (1 mg/kg, i.p. t=−30 min) or the κ-selective antagonist, nor-BNI (30 mg/kg, i.p. t=−24 h) prior to an s.c. injection with an $ED_{90}$ dose of UMB 425 (15 mg/kg). Latencies were determined 30 min after UMB 425 administration.
Figure 3:
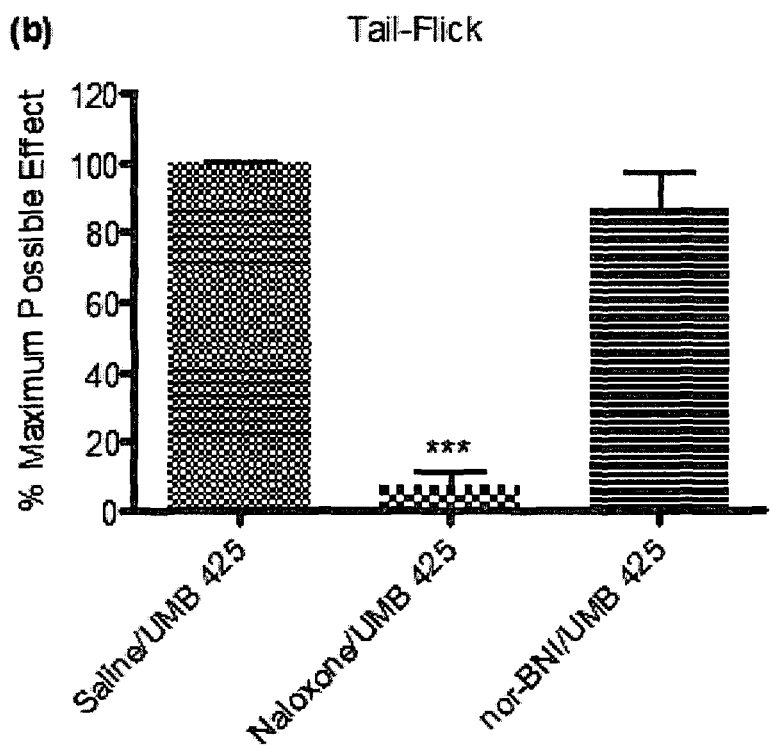

To corroborate opioid-induced antinociception, various antagonist pretreatments were given in conjunction with UMB 425 administration. One-way analysis of variance (ANOVA) indicated differences amongst mice pretreated with saline, naloxone and nor-BNI (F(2,12)=8.88, p<0.005; F(2,13)=22.61, p<0.0001 for the hot plate and tail-flick assays, respectively). UMB 425's partial agonistic effects through the μ receptor appear primarily responsible for the observed antinociceptive effects seen in vivo as naloxone significantly attenuated UMB 425-mediated antinociception (FIG. 3; q=4.55, p<0.05; q=8.48, p<0.001 for the hot plate and tail-flick assays, respectively; Tukey's post-hoc). In contrast, pretreatment with the κ antagonist nor-BNI failed to significantly attenuate UMB 425-mediated antinociception (FIG. 3; q=0.01, n.s.; q=1.39, n.s. for the hot plate and tail-flick assays, respectively; Tukey's post-hoc). Consistent with the lack of agonist activity observed in the [$^{35}$S]GTPγS assay at κ receptors by UMB 425, the κ receptor does not appear to contribute significantly to the antinociceptive effects of UMB 425.

Tolerance to Antinociceptive Effects.

Figure 4:
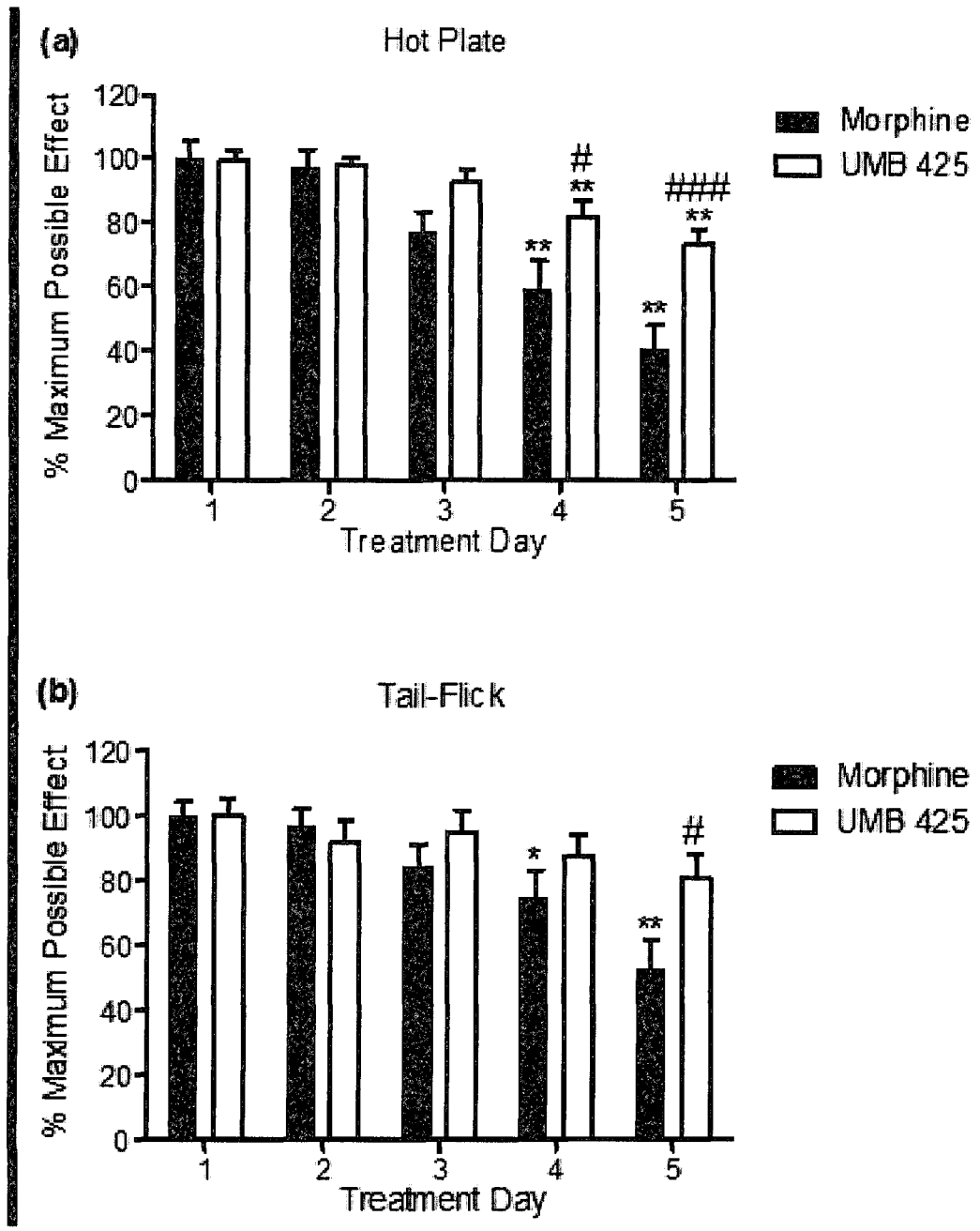
FIG. 4. Antinociceptive tolerance development for morphine and UMB 425 for the hot plate and tail-flick assays. Male, Swiss-Webster mice were given an $ED_{90}$ dose of morphine (15 mg/kg, s.c.) or UMB 425 (15 mg/kg, s.c.) twice daily for a five day period. Latencies were determined 30 min after drug administration.
Figure 5:
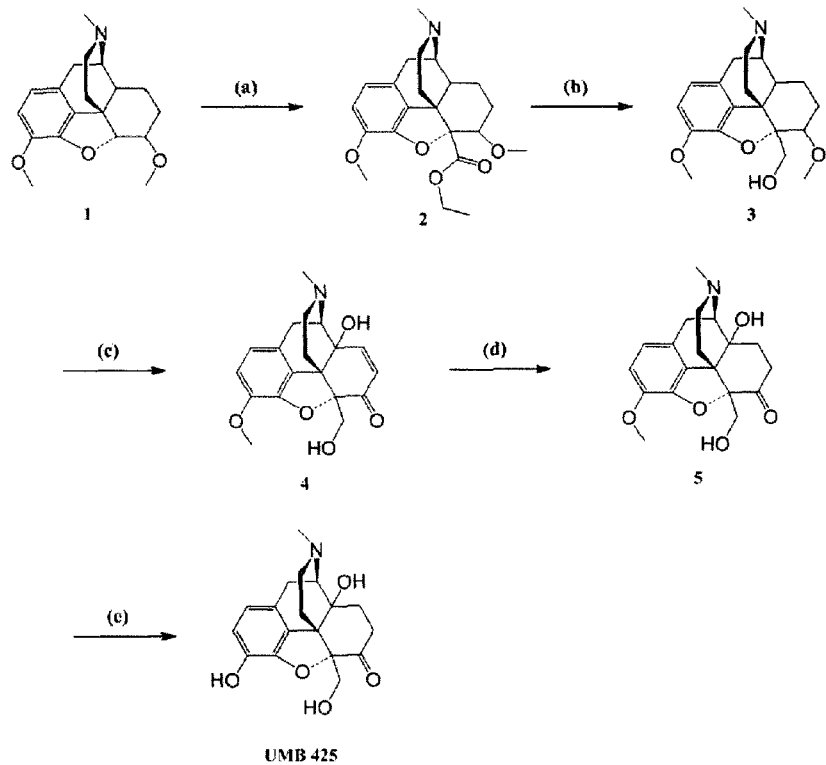
FIG. 5. Chemical synthesis of UMB 425 from thebaine.
Figure 6:
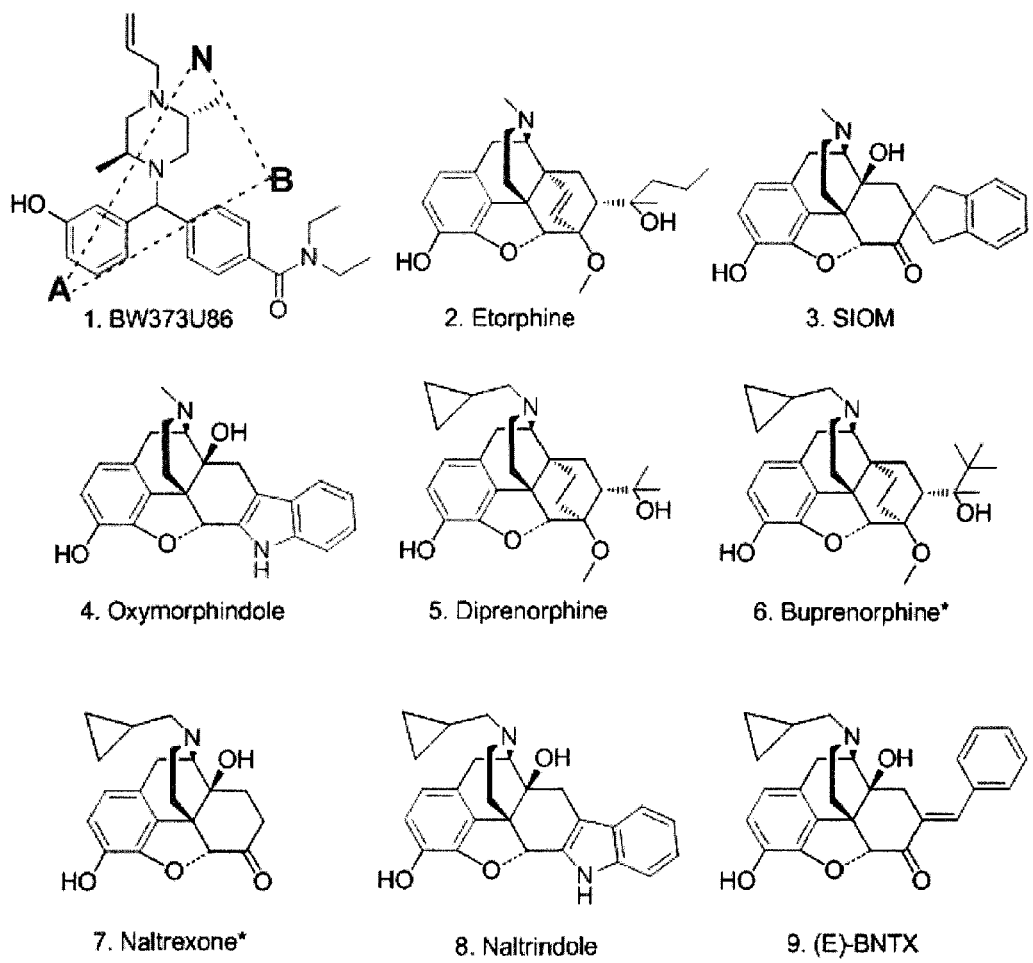
FIG. 6. Compounds included in the δ receptor CSP training set.
Figure 7:
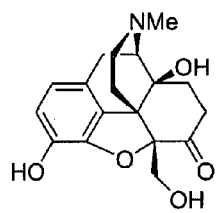
FIG. 7. Novel opioid narcotics: UMB 425, oxycodone analog, analogs of morphine, dihydromorphine, hydromorphone, codeine, dihydrocodeine, hydrocodone and ethylmorphine.
Figure 7:
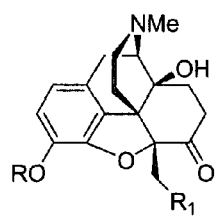
Figure 7:
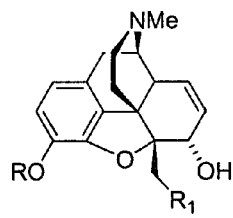
Figure 7:
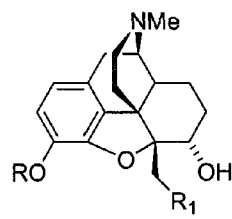
Figure 7:
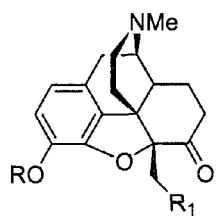

The results of administration of $ED_{90}$ doses of morphine and UMB 425 to mice twice daily for a period of five days, with test latencies determined 30 min after drug administration are summarized in FIG. 4. One-way repeated measures ANOVA demonstrated statistical differences amongst treatment days for morphine administration in both the hot plate (FIG. 4a; F(4,76)=15.22, p<0.0001) and tail-flick assays (FIG. 4b; F(4,76)=8.52, p<0.0001). Dunnett's post-hoc analysis revealed that morphine administration significantly decreased antinociceptive activity on Day 4 and 5 of the tolerance paradigm for both the hot plate (FIG. 4a; q=4.45, p<0.01; q=6.52, p<0.01; respectively) and tail-flick assays (FIG. 4b; q=2.72, p<0.05; q=5.12, p<0.01; respectively). One-way repeated measures ANOVA also demonstrated statistical difference amongst treatment days for UMB 425 administration in the hot plate assay (FIG. 4a; F(4,84)=9.32, p<0.0001) but not for the tail-flick assay (FIG. 4b, F(4,76)=1.53, n.s.). Dunnett's post-hoc analysis revealed that UMB 425 administration significantly decreased antinociceptive activity on Day 4 and 5 of the tolerance paradigm in the hot plate assay (FIG. 4a; q=3.43, p<0.01; q=5.11, p<0.01; respectively).

Two-way repeated measures ANOVA revealed statistical differences between morphine and UMB 425 treatment in time points for both the hot plate (FIG. 4a; p<0.0001) and tail flick assays (FIG. 4b; p<0.0001). Bonferroni's post-hoc analysis demonstrated that UMB 425 maintained statistically greater antinociceptive activity than morphine on Day 4 and 5 for the hot plate assay (FIG. 4a; t=2.86, p<0.05; t=4.15, p<0.001; respectively) and on Day 5 for the tail-flick assay (FIG. 4b; t=2.88, p<0.05).

Our tolerance paradigm involves thermal nociceptive testing on a daily basis to ensure that a statistical difference in antinociceptive activity is seen between morphine and UMB 425 prior to a dose-response challenge. Table 5 summarizes respective $ED_{50}$ values for morphine and UMB 425 from the dose-response challenge on Day 6 of the tolerance paradigm. UMB 425 ($ED_{50}$=12.96 and 11.58 mg/kg for the hot plate and tail-flick assays, respectively) produced markedly less tolerance development than morphine ($ED_{50}$=21.31 and 44.11 mg/kg for the hot plate and tail-flick assays, respectively), as evident by the respective rightward shifts in $ED_{50}$ values (7.8- vs. 3.0-fold and 6.4- vs. 1.3-fold for morphine vs. UMB 425 in the hot plate and tail-flick assays, respectively). Respective $ED_{50}$ shifts in the morphine-treated tolerance paradigm seen on Day 6 were comparable to tolerance paradigms previously performed using male ICR mice, despite variations regarding drug dosing, route of administration, number of injections per day as well as the time length of the paradigm (33)

The antagonistic potency of UMB 425 through the δ receptor ($pA_2$=6.12) is lower than previously highlighted μ agonist/δ antagonist analgesics, notably 17d (δ $K_e$=0.091±0.01 nM) (34), as well as the δ-selective antagonist naltrindole ($pA_2$=10.92) (32). Yet, UMB 425 demonstrated a significant reduction in tolerance liabilities compared to morphine itself, specifically a 2.6- and 4.9-fold reduction in respective $ED_{50}$ shifts for the hot plate and tail-flick assays. The recently reported mixed μ agonist/δ antagonist analgesic 17d was found to have a 5.6-fold decrease in respective $A_{50}$ shifts compared to morphine itself in the warm-water tail-withdrawal assay (34). The respective shift-fold variations between the in vivo studies are thus quite comparable despite the lower affinity and antagonist potency of UMB 425 compared to 17d for the δ receptor in vitro. Thus, equipotence at the μ and δ receptor does not seem required to improve tolerance liabilities of opioid analgesics.

The pharmacological effects of UMB 425 seen in vivo are good. Further testing may assess other potential side effects including respiratory depression, decreased gastrointestinal motility, physical as well as psychological dependence. It is noteworthy that δ antagonists and δ opioid receptor knockout mice have been shown in earlier studies to attenuate the rewarding effects of morphine (35, 36), reduce respiratory depression liabilities associated with fentanyl analogs (37) and promote colonic propulsion (38). In addition, mixed μ agonist/δ antagonist analgesics have been shown to reduce physical dependence (33).

The molecular mechanisms surrounding opioid-induced tolerance are still not clear, although many efforts have been taken to discern the labyrinth of potential components involved. Morphine, a partial μ agonist, is unable to properly internalize the μ receptor upon activation, whereby desensitization and uncoupling of the G-protein potentially leads to the development of tolerance (39). δ receptor recruitment to the plasma membrane has been shown to increase with extended exposure to μ agonists (40). Furthermore, δ antagonists can provide synergistic effects in combination with μ agonists that enhances μ receptor binding and signaling in cells expressing μ-δ hetero-dimers, potentially through altered G-protein activation (41). It is conceivable that the μ agonist/δ antagonist interactions through UMB 425 allow for proper internalization, driven by the δ receptor in the hetero-oligomeric complex, and subsequent μ receptor mediated recycling and resensitization thereby leading to reduced tolerance development. Further studies may delineate the underlying mechanisms through which UMB 425 reduces the development of tolerance compared to morphine.

In summary, UMB 425 is a novel opioid mixed μ agonist/δ antagonist that possesses antinociceptive effects comparable to morphine with reduced tolerance liabilities. It has nanomolar affinity and efficacy for μ receptors similar to morphine and moderate affinity for δ receptors at which it exhibits antagonistic effects. UMB 425 is structurally similar to traditional μ agonists, and CSP models suggest that its hydroxyl moiety assumes conformations that allow interactions similar to orvinols with mixed μ agonist/δ antagonist effects. Together, the data suggest that traditional δ selective motifs need not be added to a traditional μ agonist pharmacophore to achieve δ antagonism and reduce opioid-induced tolerance.

Methods

Chemical Synthesis.

All reagents and solvents were purchased from Sigma-Aldrich, and used without further purification. NMR spectra were recorded on a Varian Mercury 400 system (400 MHz for $^1$H and 100 MHz for $^{13}$C NMR), using $CDCl_3$ or $CD_3OD$ as a solvent. Mass spectra were determined using a Bruker Amazon X Ion Trap spectrometer. Melting points are uncorrected. Purification was performed by column chromatography over Whatman silica gel 60 (230-400 mesh) using dichloromethane and methanol. Reactions were monitored by TLC using dichloromethane/methanol (92:8).

Ethyl 7,9-dimethoxy-3-methyl-2,3,4,7a-tetrahydro-1H-4,12-methanobenzofuro[3,2-e]isoquinoline-7a-carboxylate (2)

A solution of 1 g of thebaine 1 in 20 mL of tetrahydrofuran (THF) was placed in a flame-dried round-bottom flask, and 1.92 mL (1.5 equiv) of a 2.5 M solution of N-butyllithium in hexane was added while stirring at −78° C. under nitrogen. The mixture immediately turned deep wine-red and was stirred for 45 min at −78° C. Ethyl chloroformate (0.36 mL, 1.2 equiv) was added and the mixture was stirred for 4 h at −78° C. The color changed to orange-yellow. Saturated $NH_4Cl$ (5 mL) was then added per drop and most part of the solvent was removed under reduced pressure. The residual brown product was dissolved in chloroform, washed with brine solution, dried ($Na_2SO_4$) and concentrated. The residue was subjected to column chromatography on silica gel using dichloromethane-methanol (95:5) as the eluent to isolate 0.786 g (64% yield) of 5-carbethoxythebaine 2 as a pale yellow foam. $^1$H NMR ($CDCl_3$, 400 MHz): δ 6.67 d (1H, J=8.6 Hz), 6.61 d (1H, J=8.6 Hz), 5.2 d (1H, J=6.2 Hz), 5.19 d (1H, J=6.2 Hz), 4.44-4.33 m (1H), 4.28-4.16 m (1H), 3.85 s (3H), 3.66 d (1H, J=6.2 Hz), 3.57 s (3H), 3.29 d (1H, J=17.9 Hz), 2.87-2.74 m (1H), 2.7 d (1H, J=7.0 Hz), 2.68-2.57 m (1H), 2.45 s (3H), 2.16 td (1H, J=4.6, 12.5 Hz), 1.64 d (1H, J=13.3 Hz), 1.30 t (3H, J=7.0 Hz). $^{13}$C NMR ($CDCl_3$, 100 MHz): δ 168.31, 152.64, 143.62, 142.66, 132.30, 130.56, 127.38, 119.86, 113.44, 112.09, 97.05, 95.42, 61.80, 61.26, 56.45, 55.27, 49.09, 45.49, 42.12, 31.01, 30.42, 14.21. MS (ESI): m/z 384.1 $(M+1)^+$.

7,9-dimethoxy-3-methyl-2,3,4,7a-tetrahydro-1H-4,12-methanobenzofuro[3,2-e]isoquinolin-7a-yl)methanol (3)

Lithium aluminum hydride (LAH) (0.00496 g, 0.13 mmol) was added to a stirred solution of 5-carbethoxythebaine 2 (0.050 g, 0.13 mmol) in dry THF (2 mL) at 0° C. and allowed to warm to room temperature. After 2 h, the reaction mixture was quenched with saturated sodium sulfate solution and stirred for 30 min. The reaction mixture was filtered through celite; the organic layer was separated, concentrated and purified by silica gel column chromatography (15:85 methanol-dichloromethane) to yield the pure product 5-(hydroxymethyl) thebaine 3 as a pale yellow solid (0.036 g, 81% yield) with mp 169-171° C. $^1$H NMR (CDCl$_3$, 400 MHz): δ 6.62 d (1H, J=7.8 Hz), 6.58 d (1H, J=7.8 Hz), 5.57 d (1H, J=6.2 Hz), 5.19 d (1H, J=6.2 Hz), 4.26 d (1H, J=10.9 Hz), 4.07 d (1H, J=11.7 Hz), 3.79 s (3H), 3.66 d (1H, J=6.2 Hz), 3.55 s (3H), 3.32 d (1H, J=17.9 Hz), 2.90-2.79 m (1H), 2.78-2.66 m (2H), 2.53 td (1H, J=4.6, 12.5 Hz), 2.46 s (3H), 1.8 d (1H, J=12.5 Hz). $^{13}$C NMR (CDCl$_3$, 100 MHz): δ 153.13, 143.21, 142.58, 133.86, 130.59, 126.59, 119.64, 113.08, 112.36, 98.34, 94.0, 61.68, 61.48, 56.08, 55.17, 47.19, 45.27, 41.63, 31.25, 28.32. MS (ESI): m/z 342.2 (M+1)$^+$.

4a-hydroxy-7a-(hydroxymethyl)-9-methoxy-3-methyl-2,3,4,4a-tetrahydro-1H-4,12-methanobenzofuro[3,2-e]isoquinolin-7(7aH)-one (4)

An ice-cold mixture of 0.4 mL of 0.7% H$_2$SO$_4$, 0.125 mL of 88% HCO$_2$H, and 0.251 mL of 30% H$_2$O$_2$ was added to 0.3 g (0.879 mmol) of 5-(hydroxymethyl) thebaine 3. The mixture was stirred at 0° C. until it became transparent (~30 min). The resulting solution was kept for 70 h in a refrigerator (4° C.), then poured into 3 mL of ice water alkylated by the addition of concentrated ammonia solution. The mixture was extracted with five portions of chloroform and the organic extracts were combined, dried over sodium sulfate, and evaporated to obtain 0.184 g (61%) of 5-(hydroxymethyl)-14-hydroxycodeinone 4 as a white solid with mp 231-233° C. $^1$H NMR (CDCl$_3$, 400 MHz): δ 6.69-6.55 m (3H), 6.17 d (1H, J=9.3 Hz), 4.19 d (1H, J=10.1 Hz), 4.05 d (1H, J=10.1 Hz), 3.78 s (3H), 3.22 d (1H, J=17.9 Hz), 3.18-3.1 m (1H), 2.84-2.53 m (3H), 2.48 s (3H), 2.34-2.22 m (1H), 1.57 d (1H, J=10.1 Hz). $^{13}$C NMR (CDCl$_3$, 100 MHz): δ 198.06, 146.15, 143.18, 142.85, 134.36, 130.72, 124.2, 119.83, 114.77, 91.83, 67.57, 63.46, 60.15, 56.57, 47.6, 45.37, 42.3, 25.56, 22.4. MS (ESI): m/z 344.2 (M+1)$^+$.

4a-hydroxy-7a-(hydroxymethyl)-9-methoxy-3-methyl-2,3,4,4a,5,6-hexahydro-1H-4,12-methanobenzofuro[3,2-e]isoquinolin-7(7aH)-one (5)

To a solution of 5-(hydroxymethyl)-14-hydroxycodeinone 4 (0.13 g, 0.379 mmol) in 5 mL of 1:1 ethanol-glacial acetic acid Pd/C (10%, 15 mg) was added. The mixture was evacuated and filled with H$_2$ gas in a hydrogenation flask and maintained under 40 psi H$_2$ pressure for 4 h. The reaction mixture was filtered through celite, the solvent was evaporated and the residue was basified with aqueous ammonia prior to CHCl$_3$ extraction. Organic phases were combined, washed with brine, dried over anhydrous Na$_2$SO$_4$ and the solvent was evaporated. The residue was subjected to column chromatography (7:93 methanol-dichloromethane) to give the pure olefin reduced compound 5 as white foam (0.0915 g, 70%). $^1$H NMR (CDCl$_3$, 400 MHz): δ 6.7 d (1H, J=8.6 Hz), 6.65 d (1H, J=8.6 Hz), 4.16 d (1H, J=10.9 Hz), 4.01 d (1H, J=11.7 Hz), 3.86 s (3H), 3.16 d (1H, J=18.7 Hz), 3.07 td (1H, J=5.4, 14.8 Hz), 2.96 d (1H, J=5.4 Hz), 2.67-2.51 m (2H), 2.43 s (3H), 2.40-2.29 m (2H), 2.25-2.15 m (1H), 1.96-1.87 m (1H), 1.74-1.63 m (1H), 1.47 d (1H, J=12.5 Hz). $^{13}$C NMR (CDCl$_3$, 100 MHz): δ 210.47, 144.17, 142.88, 129.60, 124.43, 119.64, 114.49, 96.26, 70.29, 64.20, 61.74, 56.53, 50.58, 44.67, 42.65, 37.31, 31.21, 26.88, 21.91. MS (ESI): m/z 346.1 (M+1)$^+$.

4a,9-dihydroxy-7a-(hydroxymethyl)-3-methyl-2,3,4,4a,5,6-hexahydro-1H-4,12-methanobenzofuro[3,2-e]isoquinolin-7(7aH)-one (UMB 425)

Compound 5 (0.104 g, 0.3 mmol) was dissolved in 2 mL CHCl$_3$ and cooled to −20° C., followed by the slow addition of BBr$_3$ solution (1 M in CHCl$_3$, 1.5 mL). The mixture was stirred at −20° C. for 3 h, carefully quenched with ice and basified with ammonia solution. The resulting mixture was stirred for 30 min at 0° C., the aqueous layer was separated and the aqueous phase was extracted with CHCl$_3$ (3×10 mL). The organic phases were combined, washed with brine and dried over sodium sulfate and the solvent was evaporated. The residue was subjected to column chromatography (20:80 methanol-dichloromethane) to obtain 5-(hydroxymethyl)-14-hydroxymorphinone UMB 425 as an off-white solid (0.0638 g, 64%) with mp 193-195° C. $^1$H NMR (CD$_3$OD, 400 MHz): δ 6.6 d (1H, J=8.1 Hz), 6.56 d (1H, J=8.1 Hz), 5.46 br s (1H), 4.23 d (1H, J=11.9 Hz), 4.0 d (1H, J=11.9 Hz), 3.16 d (1H, J=18.9 Hz), 3.12-3.01 m (1H), 2.97-2.9 m (1H), 2.62-2.49 m (2H), 2.41 s (3H), 2.4-2.33 m (1H), 2.25-2.13 m (2H), 1.91-1.83 m (1H), 1.69-1.59 m (1H), 1.33 d (1H, J=12.4 Hz). $^{13}$C NMR (CD$_3$OD, 100 MHz): δ 212.7, 144.6, 140.7, 130.9, 125.3, 120.8, 119.2, 99.20, 71.94, 65.92, 62.47, 52.62, 46.05, 42.89, 37.32, 33.49, 27.34, 23.01. MS (ESI): m/z 332.1 (M+1)$^+$.

CSP Modeling Calculations.

Quantitative conformationally sampled pharmacophore (CSP) models developed for μ and δ receptor ligands were used for studies herein (21, 22), with some modifications to the δ receptor model. Updating of the δ receptor model was performed prior to predictions of efficacy of UMB 425. As this invention involved derivates of 4,5-epoxymorphinans, the training set was limited to small non-peptidic opioids: BW373U86, etorphine, SIOM (7-spiroindanyloxymorphone), oxymorphindole, diprenorphine, buprenorphine, naltrexone, naltrindole and (E)-BNTX [(E)-benzylidenenaltrexone]. Figure S1 of the supporting information shows the chemical structures of compounds used as the training set and their experimental efficacies measured in earlier reported [$^{35}$S]GTPγS assays (29). For updating the δ receptor CSP model, the selected ligands were modeled using the CHARMM22/CMAP (42-44) and CHARMM General Force Field (CGenFF) (45) with Replica Exchange Molecular Dynamics (REX-MD) (46, 47) for conformational sampling, as previously described (21, 48). Pharmacophoric descriptors were designated for calculations of distances and angles between varying functional groups and are identified as an aromatic ring (A), a basic nitrogen (N) and a hydrophobic group (B) (Figure S1, supporting information). BW373U86 was used as the reference compound for model development. Statistical models were trained using both agonists and antagonists to differentiate overlapping patterns between the two classes of compounds as well as develop a model that allows for quantitative estimations of efficacy. Changes with respect to the original δ receptor model, include: 1) for BW373U86, the center of mass of the two piperazine nitrogen groups was designated the N phaunacophoric descriptor, and 2) 1D overlap coefficients with respect to the reference compound were used to obtain multiple regression models with two independent variables; tests using three independent variables did not lead to significant improvements in the models.

Pharmacology

Animals.

Male, Swiss-Webster mice (21-30 g, Harlan, Indianapolis, Ind.; Frederick, Md.) were housed in groups of five in polysulfone cages (Techniplast, Philadelphia, Pa.) with a 12:12-h light/dark cycle with food and water ad libitum. Animals were acclimated one week prior to experimental use and randomly assigned to treatment groups. All procedures were performed in accordance to the Institutional Animal Care and Use Committee at the West Virginia University Health Sciences Center.

Chemicals.

Dulbecco's modified Eagle's medium (DMEM) and Dulbecco's modified Eagle's medium: Nutrient Mixture F12 with Hepes 1:1 (DMEM:F12) were purchased from Fisher Scientific (Hanover Park, Ill.). Fetal bovine serum (FBS) was purchased from Atlanta Biologicals (Lawrenceville, Ga.). Penicillin-streptomycin solution (10,000 units/ml), trypsin-EDTA (0.05% trypsin) and G418 (Geneticin) 50 mg/ml were purchased from Invitrogen (Carlsbad, Calif.). Morphine sulfate, [D-Ala$^2$, N-MePhe$^4$, Gly-ol]-enkephalin (DAMGO), [D-Pen$^{2,5}$]-enkephalin (DPDPE), N-methyl-2-phenyl-N-[(5R,7S,8S)-7-(pyrrolidin-1-yl)-1-oxaspiro[4.5]dec-8-yl]acetamide (U69,593), naloxone, norbinaltorphimine (nor-BNI), guanosine 5'-diphosphate sodium salt, polyethyleneimine (PEI) and Trizma® pre-set crystals were obtained from Sigma Aldrich (St. Louis, Mo.). GTPγS lithium salt was obtained from Tocris Bioscience (Ellisville, Mo.). [$^3$H]DAMGO, [$^3$H]DPDPE, [$^3$H]U69,593 and [$^{35}$S]GTPγS were purchased from Perkin Elmer (Shelton, Conn.).

Binding Studies.

Chinese hamster ovary (CHO) cells stably transfected with and overexpressing the human μ opioid receptor (hMOR-CHO), the human δ opioid receptor (hDOR-CHO) or the human κ opioid receptor (hKOR-CHO) were grown in 150-mm dishes (Fisher Scientific, Hanover Park, Ill.) in DMEM supplemented with 10% FBS, penicillin-streptomycin and G418 at 37° C. in a 5% $CO_2$ atmosphere. Specifically, DMEM:F12 (1:1) with HEPES, L-Gln solution was used when preparing hMOR-CHO and DMEM 4.5 g/l glucose was used when preparing hDOR-CHO and hKOR-CHO. At 80-90% confluency, cells were scraped from dishes and centrifuged at 2200 RPM for 12 min at 4° C. Cell pellets were resuspended in 50 mM Tris buffer, pH 7.7, and homogenized using a polytron, then spun down twice more at 13500 RPM for 20 min at 4° C. Membrane was suspended in 50 mM Tris buffer, pH 7.7, at protein concentrations of about 3 mg/mL for hMOR-CHO and hKOR-CHO and 4 mg/mL for hDOR-CHO. Membranes were aliquoted into polypropylene tubes and frozen at −80° C. for future use. Protein concentration was determined using bicinchoninic acid (BCA) reagent and bovine serum albumin (BSA) protein standard provided by the manufacturer (Pierce, Rockford, Ill.).

Membranes were incubated with 10-12 concentrations of drug (0.001-100,000 nM) and radiolabeled ligand in 50 mM Tris buffer, pH 7.7, at a final volume of 1 mL. μ receptors were labeled using 1.3 nM [$^3$H] DAMGO. δ receptors were labeled using 1.2 nM [$^3$H] DPDPE. κ receptors were labeled using 1.7 nM [$^3$H] U69,593. Non-specific binding was determined using non-labeled equivalents at each receptor subtype: 10 μM DAMGO, 1 μM DPDPE and 10 μM U69,593. Each concentration was tested in triplicates of duplicates with a total volume of 1 mL for each well. Following a 60 min incubation period, reactions were terminated via rapid vacuum filtration over Perkin Elmer Unifilter®-96, GF/B filters (Fisher Scientific, Hanover Park, Ill.) that were presoaked in 0.5% polyethyleneimine (PEI) for 30 min. After filtration, filters were washed three times with 1.5 mL of cold 50 mM Tris buffer, pH 7.7 and counted in 40 μL of Perkin Elmer Microscint 20 (Fisher Scientific, Hanover Park, Ill.). Mean $K_i$ values±S.E.M. were determined performing experiments in triplicates of duplicates and calculated using $K_d$ values obtained during saturation binding assays and the Cheng-Prusoff equation.

[$^{35}$S]GTPγS Functional Assays.

Membrane preparation for [$^{35}$S]GTPγS binding was similar to the aforementioned opioid binding studies, with the exception that CHO cells expressing hMOR, hDOR and hKOR were resuspended in a final solution ("Buffer A") consisting of 100 mM NaCl, 10 mM $MgCl_2$, 20 mM Hepes, pH 7.4. Membranes were incubated with 10-12 concentrations of drug and 1 nM [$^{35}$S]GTPγS in "Buffer A" at a final volume of 1 mL. Exogenous guanosine diphosphate (GDP, 100 μL) was added to "Buffer A" per 96-well plate using a 10 mM stock that was made fresh daily. Basal activity was determined in the presence of exogenous GDP and in the absence of an agonist, while non-specific binding was determined in the presence of 10 μM unlabelled GTPγS. Following a 60 min incubation period, reactions were terminated via rapid vacuum filtration over Perkin Elmer Unifilter®-96, GF/B filters that were presoaked in a 1% BSA solution for 30 min. After filtration, filters were washed three times with 1.5 mL of cold 50 mM Tris buffer, pH 7.7 and counted in 40 μL/well of Perkin Elmer Microscint 20. Data are presented as the percentage of agonist stimulation (% $E_{max}$) of [$^{35}$S]GTPγS binding normalized against maximal stimulating concentrations of 10 μM DAMGO, 1 μM DPDPE or 10 μM U69,593. % $E_{max}$ values were determined using the equation: $[(CPM_{bound} - CPM_{basal})/(CPM_{max} - CPM_{basal})] \times 100$. Antagonistic properties at δ receptors were determined by constructing dose-response curves of DPDPE (0.01-1000 nM) in the presence and absence of UMB 425. UMB 425 concentrations were 1× (200 nM), 3× (600 nM), and 10× (2 μM) the estimated $K_i$ value obtained from binding studies. $pA_2$ values are indicative of antagonistic potency at a particular receptor subtype and were determined using a Schild plot, whereby the plot's x-intercept equals $pA_2$. Corresponding slope values at or near −1 indicate competitive antagonism for the compound at that particular receptor subtype. For compounds displaying % $E_{max}$<50, potential antagonistic properties were determined. Mean±S.E.M. were determined by performing experiments in triplicates of duplicates.

Hot Plate Antinociceptive Testing.

Mice were placed within a plastic cylinder (10.8 cm ID) atop a black anodized, aluminum plate (27.9 cm×26.7 cm×1.9 cm) uniformly regulated at 53° C. (IITC Life Science Inc., Woodland Hills, Calif.). The latency to the first sign of excessive shaking, lifting and/or licking of the hind paws was determined and recorded as the behavioral endpoint. Two baseline latencies (BL) were recorded prior to drug administration, with an average BL within 8-10 sec needed for further testing. Mice were then given subcutaneous injections of either morphine (0.1-20 mg/kg) or UMB 425 (0.1-20 mg/kg) and testing latencies (TL) for nociceptive responses were recorded at various time points thereafter. Previous studies have reported that the higher doses of morphine will induce at or near full antinociceptive activity for thermal nociceptive assays (49). A similar dosing paradigm was used for UMB 425, since in vitro opioid binding and functional data for UMB 425 were comparable to morphine. The subcutaneous route of injection was chosen because of its common usage with antinociception regimens. A 30 sec cutoff latency (CL) was predetermined so as to not cause tissue damage. Data obtained were reported as % Maximum Possible Effect (% MPE), which is indicative of antinociceptive activity associated with a particular compound. % MPE is determined using the following formula: % MPE=$[(TL-BL)/(CL-BL)] \times 100$.

Tail-Flick Antinociceptive Testing.

Mice were placed in restraints (2.5 cm ID×10.2 cm length) and their tails were placed underneath an overhead halogen light source (IITC Life Science Inc., Woodland Hills, Calif.) whereby the latency to the first sign of a rapid tail flick was determined and recorded as the behavioral endpoint. Two BL values were recorded prior to drug administration, with an average BL within 2-4 sec needed for further testing. Animals were then administered test compound at dosages reported for hot plate antinociceptive testing and TL values recorded at various time points thereafter. A 10 sec CL was predetermined so as to not cause tissue damage. % MPE values were determined as described above.

Antagonist Studies.

To determine the opioid receptors involved in the antinociceptive effects of UMB 425, mice were pretreated with the non-selective opioid antagonist naloxone (1 mg/kg i.p., t=−30 min) or the κ-selective antagonist nor-BNI (30 mg/kg i.p., t=−24 h). Antinociceptive testing was performed 30 min after subcutaneous administration of an $ED_{90}$ dose of morphine or UMB 425. The selected antagonist dosages and pretreatment time points have been shown to correspond with the intended opioid receptor subtype and peak antagonist effect (50, 51).

Tolerance Assay.

The tolerance regimen was performed using previously published methods, with some modifications (33, 49). Mice were administered twice daily (8 AM and 8 PM) subcutaneous injections of a test compound at respective $ED_{90}$ doses for a five day period. On Day 6, animals were given varying doses of morphine (0.1-20 mg/kg) or UMB 425 (0.1-20 mg/kg) and antinociceptive activity was determined using both the hot plate and tail-flick assays to determine tolerance development. Respective $ED_{50}$ values determined during the tolerance assay were then compared to values obtained in the acute treatment paradigm. On Days 1-5, the order of the antinociceptive measurements were counterbalanced so that half the mice were assessed for hot plate latencies in the AM and tail-flick latencies in the PM; the other half were tested for tail-flick latencies in the AM and hot plate latencies in the PM. On Day 6, animal test latencies were determined, first with the tail-flick assay followed 15 min later by the hot-plate assay.

Statistical Analysis.

Graphpad Prism software (San Diego, Calif.) was used for all statistical analysis. Opioid binding and [$^{35}$S]GTPγS binding data analysis was performed using a non-linear regression binding model. $K_i$, $EC_{50}$, % $E_{max}$ and $pA_2$ values were determined as described above. For in vivo antinociceptive assays, agonist $ED_{50}$ values were calculated using a non-linear regression model. For antagonist studies, a one-way analysis of variance (ANOVA) followed by Tukey's post-hoc tests were used to determine significance between groups. For the tolerance assay, repeated measures one-way ANOVA followed by Dunnett's post-hoc tests were used to determine significance between treatment days for test compound treatment. Repeated measures two-way ANOVA and Bonferroni's post-hoc tests were used to determine significance between groups. For all comparisons, p<0.05 was considered statistically significant.

Abbreviations

ANOVA, analysis of variance; BCA, bicinchoninic acid; BL, baseline latencies; BSA, bovine serum albumin; BW373U86, (±)-4-((α-R*)-α-((2S*,5R*)-4-Allyl-2,5-dimethyl-1-piperazinyl)-3-hydroxybenzyl)-N,N-diethyl-benzamide; CHO, Chinese hamster ovary; CL, cutoff latency; CPM, counts per minutes; CSP, conformationally sampled pharmacophore; DAMGO, [D-Ala$^2$, N-MePhe$^4$, Gly-ol]-enkephalin; DMEM, Dulbecco's modified Eagle's medium; DPDPE, [D-Pen$^{2,5}$]-enkephalin; (E)-BNTX, [(E)-benzylidenenaltrexone]; FBS, fetal bovine serum; GDP, guanosine diphosphate; hDOR, human δ opioid receptor; hKOR, human κ opioid receptor; hMOR, human μ opioid receptor; i.p., intraperitoneal; LAH, lithium aluminum hydride; MPE, maximum possible effect; nor-BNI, norbinaltorphimine; Pd/C, palladium on carbon; s.c., subcutaneous; S.E.M., standard error of the mean; SIOM, 7-spiroindanyloxymorphone; TL, testing latencies; THF, tetrahydrofuran; U69,953, N-methyl-2-phenyl-N-[(5R,7S,8S)-7-(pyrrolidin-1-yl)-1-oxaspiro[4.5]dec-8-yl]acetamide; UMB 425, 4a,9-dihydroxy-7a-(hydroxymethyl)-3-methyl-2,3,4,4a,5,6-hexahydro-1H-4,12-methanobenzofuro[3,2-e]isoquinolin-7(7aH)-one.

TABLE 1

Top five δ receptor conformationally sampled pharmacophore models that define the final predictive model.

| Model # | a | $X_1$ | b | $X_2$ | c | $R^2$ | p-value | Correlation Coefficient |
|---|---|---|---|---|---|---|---|---|
| 1 | 0.465 | AB | 0.514 | BN | 0.028 | 0.962 | 0.00005 | 0.815 |
| 2 | 0.730 | AB | 0.235 | ANB | −0.031 | 0.919 | 0.00054 | 0.519 |
| 3 | 0.760 | AB | 0.187 | BAN | −0.026 | 0.911 | 0.00071 | 0.442 |
| 4 | 0.749 | AB | 0.182 | ABN | −0.037 | 0.893 | 0.00121 | 0.603 |
| 5 | 1.094 | BN | −0.196 | ANB | 0.108 | 0.890 | 0.00133 | 0.797 |

Multiple regression equations, efficacy=$aX_1+bX_2+c$. N represents the basic nitrogen, A is the aromatic ring and B is the hydrophobic group, as shown in Figure S1 of the supporting information. $X_1$ and $X_2$ are overlap integrals with respect to the reference compound, while a and b are coefficients for variables $X_1$ and $X_2$ and c is the y-intercept in the regression equations. $R^2$ is the goodness of fit, p-value the significance of models and correlation coefficients between $X_1$ and $X_2$ overlap coefficients.

TABLE 2

Comparison between experimental and calculated efficacy values for compounds in training set.

| | Relative % $E_{max}$ | |
|---|---|---|
| Name | Experimental | Calculated |
| BW373U86 | 1.00 | 0.96 |
| Etorphine | 0.36 | 0.36 |
| SIOM | 0.18 | 0.13 |
| Oxymorphindole | 0.12 | 0.04 |
| Diprenorphine | 0.08 | 0.01 |
| Buprenorphine | 0.00 | 0.13 |
| Naltrexone | 0.00 | 0.01 |
| Naltrindole | 0.00 | 0.04 |
| (E)-BNTX | 0.00 | 0.07 |

Experimental data, except buprenorphine and naltrexone, is previously reported (29). Buprenorphine and naltrexone were experimentally designated % $E_{max}$=0 values as both are classified as antagonists at the δ receptor (5, 24). BW373U86= (±)-4-((α-R*)-α-((2S*,5R*)-4-Allyl-2,5-dimethyl-1-piperazinyl)-3-hydroxybenzyl)-N,N-diethyl-benzamide, SIOM=7-spiroindanyloxymorphone, (E)-BNTX=[(E)-benzylidenenaltrexone].

TABLE 3

In vitro pharmacological profiles of morphine and UMB 425.

| | $K_i$ ± S.E.M. (nM) | | | $EC_{50}$ ± S.E.M. (nM) | | | % $E_{max}$ ± S.E.M. | | | $pA_2$ |
|---|---|---|---|---|---|---|---|---|---|---|
| | μ | δ | κ | μ | δ | κ | μ | δ | κ | δ |
| Morphine | 1.7 ± 0.34 | 87 ± 6.6 | 69 ± 1.3 | 38 ± 4.9 | 316.5 ± 4.9$^a$ | 484 ± 213$^a$ | 81 ± 2.3 | 103 ± 7$^a$ | 62 ± 7$^a$ | nd |
| UMB 425 | 3.2 ± 0.14 | 208 ± 18 | 212 ± 21 | 35 ± 3.7 | n/e | n/e | 73 ± 7.3 | nd | nd | 6.12 (−0.91) |

Receptor binding and [$^{35}$S]GTPγS functional activity for morphine and UMB 425 are summarized for studies performed in CHO cell membranes stably transfected and overexpressing the human μ, δ and κ opioid receptors. Competition binding for compounds were performed in triplicate of duplicates and reported as mean $K_i$ values+S.E.M. Mean $EC_{50}$ and % $E_{max}$ values±S.E.M. for the [$^{35}$S]GTPγS functional assays were performed in triplicate of duplicates. $pA_2$ is defined as the negative logarithm of antagonist concentration needed to shift the dose response curve by a factor of 2. A slope of at or near −1 is indicative of competitive antagonism for the drug at the receptor. $^a$Ref (32). n/e=no effect, nd=not determined.

TABLE 4

$ED_{50}$ values for morphine and UMB 425 in the acute treatment paradigm.

| $ED_{50}$ (mg/kg) | Morphine | UMB 425 |
|---|---|---|
| Hot Plate | 2.73 | 4.30 |
| Tail-Flick | 6.85 | 8.83 |

Summary of antinociceptive activity of acute morphine (0.1-20 mg/kg, s.c.) and UMB 425 (0.1-20 mg/kg, s.c.) treatment in Swiss, Webster mice for the hot plate and tail-flick assays. Respective $ED_{50}$ values (in mg/kg, s.c.) were obtained at the 30 min time point after drug administration.

TABLE 5

$ED_{50}$ values for morphine and UMB 425 in the tolerance treatment paradigms.

| | Morphine | | UMB 425 | |
|---|---|---|---|---|
| $ED_{50}$ (mg/kg) | Tolerance | Shift | Tolerance | Shift |
| Hot Plate | 21.31 | 7.8 | 12.96 | 3.0 |
| Tail-Flick | 44.11 | 6.4 | 11.58 | 1.3 |

Summary of antinociceptive activity obtained for the tolerance paradigm for morphine and UMB 425 for the hot-plate and tail-flick assays. Mice were treated with the $ED_{90}$ dose of morphine (15 mg/kg, s.c.) or UMB 425 (15 mg/kg, s.c.) determined in the acute treatment paradigm, twice a day for five days. $ED_{50}$ values for the tolerance paradigm were obtained during a dose-response challenge on Day 6 of treatment, whereby latencies were determined 30 min after drug administration (tolerance columns). The shifts represent fold-shifts in the $ED_{50}$ determined in the acute vs. tolerance treatment paradigms.

REFERENCES

1. Stein, C. (1995) The control of pain in peripheral tissue by opioids, *N Engl J Med* 332, 1685-1690.
2. Caudill-Slosberg, M. A., Schwartz, L. M., and Woloshin, S. (2004) Office visits and analgesic prescriptions for musculoskeletal pain in US: 1980 vs. 2000, *Pain* 109, 514-519.
3. Benyamin, R., Trescot, A. M., Datta, S., Buenaventura, R., Adlaka, R., Sehgal, N., Glaser, S. E., and Vallejo, R. (2008) Opioid complications and side effects, *Pain Physician* 11, S105-120.
4. Manchikanti, K. N., Manchikanti, L., Damron, K. S., Pampati, V., and Fellows, B. (2008) Increasing deaths from opioid analgesics in the United States: an evaluation in an interventional pain management practice, *J Opioid Manag* 4, 271-283.
5. Waldhoer, M., Bartlett, S. E., and Whistler, J. L. (2004) Opioid receptors, *Annu Rev Biochem* 73, 953-990.
6. Stein, C., Schafer, M., and Machelska, H. (2003) Attacking pain at its source: new perspectives on opioids, *Nat Med* 9, 1003-1008.
7. Wang, J. B., Johnson, P. S., Persico, A. M., Hawkins, A. L., Griffin, C. A., and Uhl, G. R. (1994) Human mu opiate receptor. cDNA and genomic clones, pharmacologic characterization and chromosomal assignment, *FEBS Lett* 338, 217-222.
8. Evans, C. J., Keith, D. E., Jr., Morrison, H., Magendzo, K., and Edwards, R. H. (1992) Cloning of a delta opioid receptor by functional expression, *Science* 258, 1952-1955.
9. Mansson, E., Bare, L., and Yang, D. (1994) Isolation of a human kappa opioid receptor cDNA from placenta, *Biochem Biophys Res Commun* 202, 1431-1437.
10. Matthes, H. W., Maldonado, R., Simonin, F., Valverde, O., Slowe, S., Kitchen, I., Befort, K., Dierich, A., Le Meur, M., Dolle, P., Tzavara, E., Hanoune, J., Rogues, B. P., and Kieffer, B. L. (1996) Loss of morphine-induced analgesia, reward effect and withdrawal symptoms in mice lacking the mu-opioid-receptor gene, *Nature* 383, 819-823.
11. Horan, P., Tallarida, R. J., Haaseth, R. C., Matsunaga, T. O., Hruby, V. J., and Porreca, F. (1992) Antinociceptive interactions of opioid delta receptor agonists with morphine in mice: supra- and sub-additivity, *Life Sci* 50, 1535-1541.
12. Abdelhamid, E. E., Sultana, M., Portoghese, P. S., and Takemori, A. E. (1991) Selective blockage of delta opioid receptors prevents the development of morphine tolerance and dependence in mice, *J Pharmacol Exp Ther* 258, 299-303.
13. Hepburn, M. J., Little, P. J., Gingras, J., and Kuhn, C. M. (1997) Differential effects of naltrindole on morphine-in- 14. Schiller, P. W., Fundytus, M. E., Merovitz, L., Weltrowska, G., Nguyen, T. M., Lemieux, C., Chung, N. N., and Coderre, T. J. (1999) The opioid mu agonist/delta antagonist DIPP-NH(2)[Psi] produces a potent analgesic effect, no physical dependence, and less tolerance than morphine in rats, *J Med Chem* 42, 3520-3526.
15. Portoghese, P. S. (1989) Bivalent ligands and the message-address concept in the design of selective opioid receptor antagonists, *Trends Pharmacol Sci* 10, 230-235.
16. Daniels, D. J., Lenard, N. R., Etienne, C. L., Law, P. Y., Roerig, S. C., and Portoghese, P. S. (2005) Opioid-induced tolerance and dependence in mice is modulated by the distance between pharmacophores in a bivalent ligand series, *Proc Natl Acad Sci USA* 102, 19208-19213.
17. George, S. R., Fan, T., Xie, Z., Tse, R., Tam, V., Varghese, G., and O'Dowd, B. F. (2000) Oligomerization of mu- and delta-opioid receptors. Generation of novel functional properties, *J Biol Chem* 275, 26128-26135.
18. Morphy, R., and Rankovic, Z. (2005) Designed multiple ligands. An emerging drug discovery paradigm, *J Med Chem* 48, 6523-6543.
19. Li, T., Shiotani, K., Miyazaki, A., Tsuda, Y., Ambo, A., Sasaki, Y., Jinsmaa, Y., Marczak, E., Bryant, S. D., Lazarus, L. H., and Okada, Y. (2007) Bifunctional[2',6'-dimethyl-L-tyrosine1]endomorphin-2 analogues substituted at position 3 with alkylated phenylalanine derivatives yield potent mixed mu-agonist/delta-antagonist and dual mu-agonist/delta-agonist opioid ligands, *J Med Chem* 50, 2753-2766.
20. Ananthan, S., Khare, N. K., Saini, S. K., Seitz, L. E., Bartlett, J. L., Davis, P., Dersch, C. M., Porreca, F., Rothman, R. B., and Bilsky, E. J. (2004) Identification of opioid ligands possessing mixed micro agonist/delta antagonist activity among pyridomorphinans derived from naloxone, oxymorphone, and hydromorphone [correction of hydropmorphone], *J Med Chem* 47, 1400-1412.
21. Shim, J., Coop, A., and MacKerell, A. D., Jr. (2011) Consensus 3D model of mu-opioid receptor ligand efficacy based on a quantitative Conformationally Sampled Pharmacophore, *J Phys Chem B* 115, 7487-7496.
22. Bernard, D., Coop, A., and MacKerell, A. D., Jr. (2007) Quantitative conformationally sampled pharmacophore for delta opioid ligands: reevaluation of hydrophobic moieties essential for biological activity, *J Med Chem* 50, 1799-1809.
23. Bernard, D., Coop, A., and MacKerell, A. D., Jr. (2003) 2D conformationally sampled pharmacophore: a ligand-based pharmacophore to differentiate delta opioid agonists from antagonists, *J Am Chem Soc* 125, 3101-3107.
24. Lutfy, K., and Cowan, A. (2004) Buprenorphine: a unique drug with complex pharmacology, *Curr Neuropharmacol* 2, 395-402.
25. Gates, M., Boden, R. M., and Sundararaman, P. (1989) Derivatives of the Thebaine Anion. 2. 5-Methylmorphine, 5-Methylcodeine, 5-Methylheroin and Some Related Compounds, *J. Org. Chem.* 54, 972-974.
26. Woudenberg, R. H., Lie, T.-S., and Maat, L. (1993) Chemistry of opium alkaloids. 38. Synthesis of rigid morphinans doubly bridged at ring C, *J. Org. Chem.* 58, 6139-6142.
27. Lotfy, H. R., Schultz, A. G., and Metwally, M. A. (2003) Synthesis of 5-Methoxymethyl, 5-(2-Methoxyethyl), and 5-Allyl Thebaine, Codeinone, and Morphinone Derivatives, *Russian Journal of Organic Chemistry* 39, 1256-1260.
28. Rice, K. C. (1977) A rapid, high-yield conversion of codeine to morphine, J Med Chem 20, 164-165.
29. Clark, M. J., Emmerson, P. J., Mansour, A., Akil, H., Woods, J. H., Portoghese, P. S., Remmers, A. E., and Medzihradsky, F. (1997) Opioid efficacy in a C6 glioma cell line stably expressing the delta opioid receptor, *J Pharmacol Exp Ther* 283, 501-510.
30. Granier, S., Manglik, A., Kruse, A. C., Kobilka, T. S., Thian, F. S., Weis, W. I., and Kobilka, B. K. (2012) Structure of the delta-opioid receptor bound to naltrindole, *Nature* 485, 400-404.
31. Manglik, A., Kruse, A. C., Kobilka, T. S., Thian, F. S., Mathiesen, J. M., Sunahara, R. K., Pardo, L., Weis, W. I., Kobilka, B. K., and Granier, S. (2012) Crystal structure of the micro-opioid receptor bound to a morphinan antagonist, *Nature* 485, 321-326.
32. Toll, L., Berzetei-Gurske, I. P., Polgar, W. E., Brandt, S. R., Adapa, I. D., Rodriguez, L., Schwartz, R. W., Haggart, D., O'Brien, A., White, A., Kennedy, J. M., Craymer, K., Farrington, L., and Auh, J. S. (1998) Standard binding and functional assays related to medications development division testing for potential cocaine and opiate narcotic treatment medications, *NIDA Res Monogr* 178, 440-466.
33. Wells, J. L., Bartlett, J. L., Ananthan, S., and Bilsky, E. J. (2001) In vivo pharmacological characterization of SoRI 9409, a nonpeptidic opioid mu-agonist/delta-antagonist that produces limited antinociceptive tolerance and attenuates morphine physical dependence, *J Pharmacol Exp Ther* 297, 597-605.
34. Ananthan, S., Saini, S. K., Dersch, C. M., Xu, H., McGlinchey, N., Giuvelis, D., Bilsky, E. J., and Rothman, R. B. (2012) 14-Alkoxy- and 14-Acyloxypyridomorphinans: mu Agonist/delta Antagonist Opioid Analgesics with Diminished Tolerance and Dependence Side Effects, *J Med Chem* 55, 8350-8363.
35. Chefer, V. I., and Shippenberg, T. S. (2009) Augmentation of morphine-induced sensitization but reduction in morphine tolerance and reward in delta-opioid receptor knock-out mice, *Neuropsychopharmacology* 34, 887-898.
36. Shippenberg, T. S., Chefer, V. I., and Thompson, A. C. (2009) Delta-opioid receptor antagonists prevent sensitization to the conditioned rewarding effects of morphine, *Biol Psychiatry* 65, 169-174.
37. Su, Y. F., McNutt, R. W., and Chang, K. J. (1998) Delta-opioid ligands reverse alfentanil-induced respiratory depression but not antinociception, *J Pharmacol Exp Ther* 287, 815-823.
38. Foxx-Orenstein, A. E., Jin, J. G., and Glider, J. R. (1998) 5-HT4 receptor agonists and delta-opioid receptor antagonists act synergistically to stimulate colonic propulsion, *Am J Physiol* 275, G979-983.
39. Koch, T., and Hollt, V. (2008) Role of receptor internalization in opioid tolerance and dependence, *Pharmacol Ther* 117, 199-206.
40. Cahill, C. M., Morinville, A., Lee, M. C., Vincent, J. P., Collier, B., and Beaudet, A. (2001) Prolonged morphine treatment targets delta opioid receptors to neuronal plasma membranes and enhances delta-mediated antinociception, *J Neurosci* 21, 7598-7607.
41. Gomes, I., Jordan, B. A., Gupta, A., Trapaidze, N., Nagy, V., and Devi, L. A. (2000) Heterodimerization of mu and delta opioid receptors: A role in opiate synergy, *J Neurosci* 20, RC110.
42. Brooks, B. R., Brooks, C. L., 3rd, Mackerell, A. D., Jr., Nilsson, L., Petrella, R. J., Roux, B., Won, Y., Archontis, G., Bartels, C., Boresch, S., Caflisch, A., Caves, L., Cui, Q., Dinner, A. R., Feig, M., Fischer, S., Gao, J., Hodoscek, M., Im, W., Kuczera, K., Lazaridis, T., Ma, J., Ovchinnikov, V., Paci, E., Pastor, R. W., Post, C. B., Pu, J. Z., Schaefer, M., Tidor, B., Venable, R. M., Woodcock, H. L., Wu, X., Yang, W., York, D. M., and Karplus, M. (2009) CHARMM: the biomolecular simulation program, *J Comput Chem* 30, 1545-1614.

43. MacKerell Jr, A. D., Bashford, D., Bellott, Dunbrack, R. L., Evanseck, J. D., Field, M. J., Fischer, S., Gao, J., Guo, H., Ha, S., Joseph-McCarthy, D., Kuchnir, L., Kuczera, K., Lau, F. T. K., Mattos, C., Michnick, S., Ngo, T., Nguyen, D. T., Prodhom, B., Reiher, W. E., Roux, B., Schlenkrich, M., Smith, J. C., Stote, R., Straub, J., Watanabe, M., Wirkiewicz-Kuczera, J., Yin, D., and Karplus, M. (1998) All-Atom Empirical Potential for Molecular Modeling and Dynamics Studies of Proteins, *The Journal of Physical Chemistry* 102, 3586-3616.

44. Mackerell, A. D., Jr., Feig, M., and Brooks, C. L., 3rd. (2004) Extending the treatment of backbone energetics in protein force fields: limitations of gas-phase quantum mechanics in reproducing protein conformational distributions in molecular dynamics simulations, *J Comput Chem* 25, 1400-1415.

45. Vanommeslaeghe, K., Hatcher, E., Acharya, C., Kundu, S., Zhong, S., Shim, J., Darian, E., Guvench, O., Lopes, P., Vorobyov, I., and Mackerell, A. D., Jr. (2010) CHARMM general force field: A force field for drug-like molecules compatible with the CHARMM all-atom additive biological force fields, *J Comput Chem* 31, 671-690.

46. Sugita, Y., and Okamoto, Y. (1999) Replica-exchange molecular dynamics method for protein folding, *Chemical Physics Letters* 314, 141-151.

47. Zhou, R., Berne, B. J., and Germain, R. (2001) The free energy landscape for beta hairpin folding in explicit water, *Proc Natl Acad Sci USA* 98, 14931-14936.

48. Shim, J., and Mackerell, A. D., Jr. (2011) Computational ligand-based rational design: Role of conformational sampling and force fields in model development, *Medchemcomm* 2, 356-370.

49. Lowery, J. J., Raymond, T. J., Giuvelis, D., Bidlack, J. M., Polt, R., and Bilsky, E. J. (2011) In vivo characterization of MMP-2200, a mixed delta/mu opioid agonist, in mice, *J Pharmacol Exp Ther* 336, 767-778.

50. Heyman, J. S., Koslo, R. J., Mosberg, H. I., Tallarida, R. J., and Porreca, F. (1986) Estimation of the affinity of naloxone at supraspinal and spinal opioid receptors in vivo: studies with receptor selective agonists, *Life Sci* 39, 1795-1803.

51. Horan, P., Taylor, J., Yamamura, H. I., and Porreca, F. (1992) Extremely long-lasting antagonistic actions of nor-binaltorphimine (nor-BNI) in the mouse tail-flick test, *J Pharmacol Exp Ther* 260, 1237-1243.

The invention claimed is:

1. A chemical compound having formula UMB 425:

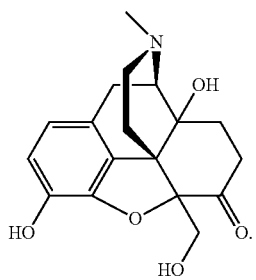

UMB 425

2. An opioid narcotic compound having a formula selected from the group consisting of Compound B and Compound C:

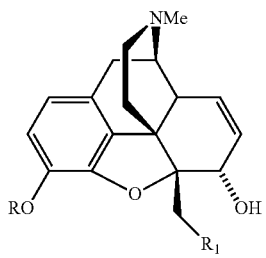

Compound B where R is hydrogen, methyl or ethyl and $R_1$ is selected from the group consisting of an alkoxy group, a halogen group, an alkylamino group, an amide group and an alkyl group;

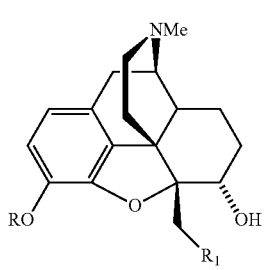

Compound C where R is hydrogen or methyl and $R_1$ is selected from the group consisting of an alkoxy group, a halogen group, an alkylamino group, an amide group and an alkyl group.

3. The opioid narcotic compound of claim 2, wherein the compound is Compound B.

4. The opioid narcotic compound of claim 2, wherein the compound is Compound C.

5. A method of treating pain comprising administering to a patient in need thereof a therapeutically effective amount of the chemical compound having formula UMB 425 of claim 1.

6. The method of treating pain of claim 5 wherein said pain is moderate-to-severe pain.

7. A method of treating pain comprising administering to a patient in need thereof a therapeutically effective amount of the chemical compound having the formula selected from the group consisting of Compound B and Compound C of claim 2.

8. The method of treating pain of claim 7 wherein said pain is moderate-to-severe pain.

9. An opioid narcotic compound having a formula selected from the group consisting of Compound A and Compound D:

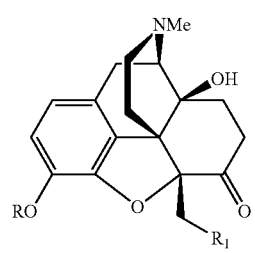

Compound A where R is methyl and $R_1$ is selected from the group consisting of an alkoxy group, a halogen group, an alkylamino group, and an amide group; and

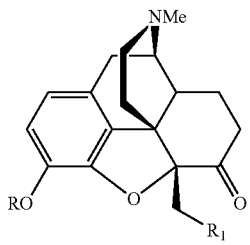

Compound D where R is hydrogen or methyl and $R_1$ is selected from the group consisting of an alkoxy group, a halogen group, an alkylamino group, and an amide group.

10. The opioid narcotic compound of claim 9, wherein the compound is Compound A.

11. The opioid narcotic compound of claim 9, wherein the compound is Compound D.

12. A method of treating pain comprising administering to a patient in need thereof a therapeutically effective amount of the chemical compound having the formula selected from the group consisting of Compound A, and Compound D of claim 9.

13. The method of treating pain of claim 12 wherein said pain is moderate-to-severe pain.

* * * * *